United States Patent [19]

Disteldorf et al.

[11] 4,454,317
[45] Jun. 12, 1984

[54] PROCESS FOR THE TRIMERIZATION OF DIISOCYANATES

[75] Inventors: Josef Disteldorf; Werner Hübel; Elmar Wolf, all of Herne, Fed. Rep. of Germany

[73] Assignee: Chemische Werke Huls Aktiengesellschaft, Marl, Fed. Rep. of Germany

[21] Appl. No.: 400,992

[22] Filed: Jul. 23, 1982

Related U.S. Application Data

[63] Continuation of Ser. No. 141,902, Apr. 21, 1980, abandoned.

[30] Foreign Application Priority Data

Apr. 21, 1979 [DE] Fed. Rep. of Germany ....... 2916201

[51] Int. Cl.$^3$ .................................. C07D 251/34
[52] U.S. Cl. .................................. 544/193
[58] Field of Search .......................... 544/193

[56] References Cited

U.S. PATENT DOCUMENTS 4,040,992 8/1977 Bechara et al. ............... 544/193

Primary Examiner—John M. Ford
Attorney, Agent, or Firm—Oblon, Fisher, Spivak, McClelland & Maier

[57] ABSTRACT

In a process for the trimerization of diisocyanates in the presence of a catalyst comprising quaternary ammonium salts of organic acids having the formula:

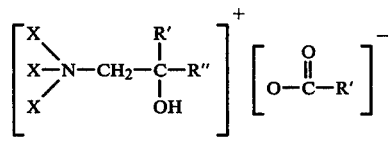

wherein X represents the same or different radicals selected from the group consisting of $C_1$–$C_{20}$ alkyl, $C_3$–$C_8$ cycloalkyl, and $C_2$–$C_{20}$ aralkyl; two X radicals taken together with at least one other heteroatom forming a hetero-ring and three X radicals taken together with the quaternary nitrogen atoms forming a hetero-ring through a common hetero-atom such that said heterocyclic ring structure is selected from the group consisting of triethylene diamine, methyl triethylene diamine, quinuclidine, N-methylmorpholine, N-ethylmorpholine, and N,N'-dimethylpiperazine; R is alkyl, cycloalkyl or aralkyl, R" is R or hydrogen; R+R" together form a $C_1$–$C_{12}$ alkyl radical; R' is hydrogen, hydroxyl or a $C_1$–$C_{12}$ alkyl radical, optionally containing a $CH_{(3-b)}Z_b$ group, wherein b=1 to 3 and Z is OH, the improvement comprising: reacting said diisocyanate with said catalyst in an amount of 0.02 to 0.1% by weight calculated on the weight of the compound to be trimerized at a temperature ranging from 40° to 120° C.

9 Claims, No Drawings

PROCESS FOR THE TRIMERIZATION OF DIISOCYANATES

This is a continuation of application Ser. No. 141,902 filed Apr. 21, 1980 now abandoned.

DESCRIPTION AND EXAMPLES

The trimerization of isocyanates is a known reaction. A multitude of chemically very different compounds are described in the literature as catalysts for the trimerization of organic isocyanates. Thus, metal compounds from the group of salts, bases, and homopolar metal compounds, such a metal naphthenates, sodium benzoate in dimethylformamide (DMF), alkaline earth acetates, formates, and carbonates, metal alkoxides, AlCl$_3$, and iron acetylacetonate can be used as trimerization catalysts. It is very difficult to separate these from the reaction products, the isocyanurates, and they can only be separated very poorly or even not at all. They just remain in the reaction products. Among the group of bases and salts, quaternary ammonium bases and quaternary ammonium salts especially have found increasing interest as trimerization catalysts for isocyanates. Thus, for example, quaternary ammonium bases are described as trimerization catalysts for isocyanates in British Pat. No. 837,120, quaternary ammonium salts of inorganic and organic O-acids having a pK of at least 2 (in aqueous solution) in U.S. Pat. No. 3,980,594, and quaternary ammonium salts from tertiary amines and α-substituted carboxylic acids in U.S. Pat. No. 3,862,150. In German Offenlegungsschrift No. 26 31 733, a process is described for carrying out condensation and/or polymerization reactions of organic isocyanates wherein a catalytic amount of a quaternary N-(hydroxyalkyl)ammonium salt having the general formula

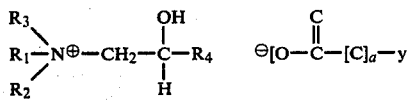

in which a represents 0 or 1; R$_1$, R$_2$, R$_3$, R$_4$ are, for example, the same or different aliphatic, cycloaliphatic, or araliphatic hydrocarbon radicals, and Y is H or alkyl, is used to promote the reaction of the organic isocyanates.

These quaternary ammonium salts are used especially in the production of foamed plastics by the reaction of aromatic diisocyanates with polyols. In contrast to most of the known catalysts proposed for the production of isocyanurate foams, those described in German Offenlegungsschrift No. 26 31 733 are conductive to a reaction of the polyol with the isocyanate which is not too rapid at the expense of the trimerization of the isocyanate. In this way, polyisocyanurate-polyurethane foams are obtained having a uniform structure (no "formation of nests").

In the case of foamed plastic produced from aromatic diisocyanates and polyols using quaternary ammonium salts, the products no longer contain reactive groups apart from small amounts of residual OH or NCO. It is, therefore, not necessary to remove the catalyst from the reaction product after the reaction is finished.

However, when producing isocyanurates through trimerization of an isocyanate having more than one NCO group in the molecule, care has to be taken to remove the trimerization catalyst from the reaction product (polyisocyanate containing isocyanurate groups) after the reaction or to deactivate it. When heated, the free NCO groups of these isocyanurates react still further in the presence of the trimerization catalyst. Macromolecular polyisocyanates are formed containing isocyanurate rings. Even cross-linking occurs with increasing reaction. From these considerations it becomes understandable why an isocyanurate which still contains catalyst and also contains NCO groups bound to the triazine ring through alkylene groups cannot be used for planned further reaction with polyols or polyamines.

It must, therefore, be the objective in any production of isocyanurates from diisocyanates to remove the catalyst completely after the trimerization is terminated. This requirement excludes the procedure of the German Offenlegungsschrift 26,31,733 as being suitable for the preparation of cold-setting, solvent-containing two-component polyurethane laquers. If one should actually attempt to trimerize aliphatic as well as aromatic diisocyanates in accordance with the teachings of German Offenlegungsschrift No. 26 31 733, it will be found that a precipitate appears when the catalyst is added to the diisocyanate. This does not disappear even upon heating to 40°–60° C.; at this temperature, isocyanurate formation proceeds with a strong evolution of heat. Under these conditions, the reaction mixture, even when strongly cooled, reaches a temperature of about 100° C. The catalyst can still be detected in the reaction product. The catalyst is bound to the reaction product as the result of an OH/NCO reaction and cannot be separated from it. It greatly impairs both the storage stability of the isocyanates containing isocyanurate groups and the intended controlled further reaction with polyols.

Furthermore, it is well known that the aliphatic or aromatic diisocyanates trimerized in accordance with the teachings of German Offenlegungsschrift No. 26 31 733 have an unpleasant amine odor. Diisocyanates can, indeed, be trimerized on a laboratory scale in accordance with the teachings of German Offenlegunsschrift No. 26 31 733. However, such trimerized diisocyanates are incompatible with the production of a solvent-containing, two-component polyurethane laquer for the reasons already discussed.

The industrial trimerization of polyisocyanates, in particular diisocyanates, in technical quantities, using the catalysts disclosed in German Offenlegungsschrift No. 26 31 733, is prevented by:

(1) the large amount of reaction heat which must be removed, and (2) the catalyst precipitate in the reaction product and the resulting effects on the trimerized diisocyanate.

It has now surprisingly been discovered that diisocyanates can be produced in substantially any industrial amount without the disadvantages pointed out for the process of German Offenlegungsschrift No. 26 31 733, by conducting the trimerization of the diisocyanates in the presence of quaternary ammonium salts of organic acids having the general formula

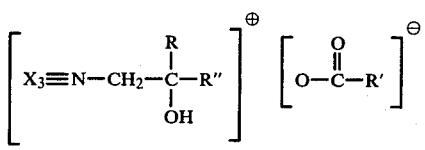

as a catalyst, wherein X represents the same or different aliphatic, cycloaliphatic, araliphatic, or heterocyclic radicals of a quaternary ammonium nitrogen atom, or a double X represents, together with the quaternary nitrogen, a ring, optionally containing one or more heteroatoms, or a triple X represents a ring formed with the quaternary nitrogen through a common heteroatom, R is a radical from the group of alkyl, cycloalkyl, and aralkyl, or R+R" together from a $C_1$-$C_{12}$-alkylradical R' is hydrogen, a hydroxyl group or a $C_1$-$C_{12}$-alkyl radical optionally containing a hydroxyalkyl group, and R" is R or hydrogen, in such a way that at most only 0.1 to 0.02 of the trimerization catalyst is used, i.e., 0.1–0.02 percent by weight, preferably 0.08–0.04 percent by weight, calculated on the weight of the compound to be trimerized, and the trimerization is conducted within a temperature range of 40°–120° C., preferably 60°–90° C.

The trimerization can then be carried out at these temperatures in a period of 1–60 minutes.

This effect was surprising and totally unexpected since, from prior experience, no catalytic activity would be expected with such a low catalyst concentration.

The compounds prepared by this trimerization process have one or more isocyanurate rings. Compounds of this type have been described in the literature.

The trimerization process can be carried out batchwise as well as continuously.

In principle, two processes can be considered for the preparation of isocyanurates free from monomer:

(1) Complete conversion of the diisocyanate and removal of the catalyst by extraction with a solvent in which the isocyanurate is practically insoluble while the diisocyanate is readily soluble; and (2) Partial conversion of the diisocyanate and removal of the unconverted diisocyanate under vacuum by thin-film distillation.

In practice, the second process has prevailed. Accordingly, in the production of diisocyanate-free isocyanurate from the diisocyanate, the diisocyanate is trimerized to an isocyanurate content which still permits handling the reaction mixture in the liquid state, and the free diisocyanate is separated in a subsequent step under vacuum by thin-film distillation.

In the batch process for trimerization of the diisocyanate in accordance with the process of the invention, the diisocyanate and 0.02–0.1 parts by weight of the specified catalyst are heated to more than 40°–60° C. but not above 120° C., preferably 70°–90° C. in a closed reaction vessel with good agitation. The course of the reaction is continuously monitored by means of the refractive index, which provides a direct measure of the degree of conversion of the diisocyanate. At a diisocyanate conversion of approximately 45%, calculated on the amount of diisocyanate used, the reaction is terminated by cooling the reaction mixture to room temperature. Such diisocyanate/isocyanurate mixtures are stable when stored at room temperature. In order to separate the unconverted, i.e., the monomeric, diisocyanate and the catalyst, the reaction mixture was then subjected to thin-film evaporation. The isocyanurates produced in this way have an NCO content of approximately 10–22% and a monomer content of <0.7%.

It has been found to be particularly advantageous to carry out the trimerization of diisocyanates in a coolable continuous reactor with continuous and sumultaneous addition of the diisocyanate and the trimerization catalyst at 40°–120° C. and during a period of 1–7 minutes. A tube-shaped reactor in the form of a reactor coil having a small diameter has proven to be very expedient in order to obtain high flow velocities. Furthermore, it is very advantageous to heat the diisocyanate/catalyst mixture to approximately 60° C. before it enters the reaction coil.

The reaction coil can also be divided, for example, into two or three zones which can be heated or cooled, if necessary, independently of each other, whereby starting material (diisocyanate+catalyst) is preheated to reaction temperature in the first zone, the reaction temperature is maintained in the second zone by partial removal of the reaction heat, and the reaction mixture is cooled down in the third zone. If the reaction mixture is to be processed immediately by thin-film distillation without intermediate storage, cooling in the third zone can be omitted.

The addition of the catalyst is critical in this continuous production of trimerized diisocyanate. It has proven to be particularly expedient to thoroughly mix the starting materials before they enter the reaction coil.

The temperatures of the reaction coil sections are appropriately selected so that the preheating zone has a temperature of approximately 40°–60° C., the reaction zone 70°–120° C., preferably 70°–90° C., and the cooling zone 20°–40° C. With a throughput of 40–120 kg/h of diisocyanate for a 0.5 cm² reactor cross-section, a diisocyanate conversion of 35–45% can easily be obtained. However, these temperature conditions must be adjusted for the conditions required by the particular diisocyanate to be trimerized.

The residence time of the diisocyanate-catalyst mixture in the reaction coil is about 1–7 minutes. Within this time approximately 35–45% of the diisocyanate is converted into the trimerized form. In order to remove the unconverted diisocyanate, the reaction mixture is then subjected to a thin-film evaporation, as already mentioned. All quaternary ammonium salts, as described in the published German Offenlegungsschrift No. 26 31 733, are suitable catalysts for the process of the invention period. It can be advantageous for a more exact metering of small amounts of catalyst to dissolve the catalyst in a suitable organic solvent. Suitable solvents are those which have no functional groups capable of reaction with the isocyanate groups under the trimerization conditions.

The process of the invention is preferably carried out substantially in the absence of solvents. The small amounts of solvents mentioned above for the purpose of dissolving the catalyst, if necessary, do not interfere with the trimerization.

Suitable starting materials which can be used in the trimerization according to the process of this invention include, for example, polyisocyanates, particularly diisocyanates, such as aliphatic, cycloaliphatic, araliphatic, i.e., aryl-substituted aliphatic, and aromatic diisocyanates, such as disclosed, for example, in Houben-Weyl, Methods of Organic Chemistry, Volume 14/2, pages 61–70, and in the article by W. Siefken in Justus Liebig's Annalen der Chemie 562, 75–136. Such diisocyanates include 1,2-ethylene diisocyanate, 1,4-tetramethylene diisocyanate, 1,6 hexamethylene diisocyanate, 2,2,4- or 2,4,4-trimethyl-1,6-hexamethylene diisocyanate (TMDI), 1,9-diisocyanato-5-methylnonane, 1,8-diisocyanato-2,4-dimethyloctane, 1,12-dodecanediisocyanate, ω,ω'-diisocyanatodipropyl ether, cyclobutene-1,3-diisocyanate, cyclohexane-1,3- and 1,4-diisocyanate, 3-aminomethyl-3,5,5-trimethylcyclohexylamine(isophoronediisocyanate(IPDI)), 1,4-diisocyanatomethyl-2,3,5,6-tetramethylcyclohexane, decahydro-8-methyl-(1,4-methanolnaphthalene-2(or 3),5-ylenedimethylenediisocyanate, hexahydro-4,7-methanoindane-1(or 2),5(or 6)-ylenedimethylenediisocyanate, hexahydro-4,7-methanoindan-1(or 2),5(or 6)-ylenediisocyanate, 2,4- and 2,6-hexahydrotoluenediisocyanate, perhydro-2,4'- and/or 4,4'-diphenylmethanediisocyanate, 4,4'-diisocyanato-3,3',5,5'-tetramethyldicyclohexylmethane, 4,4'-diisocyanato-2,2',3,3',5,5',6,6'-octamethyldicyclohexylmethane, ω,ω'-diisocyanato-1,4-diethylbenzene, 1,3- or 1,4-phenylenediisocyanate, 1,4-diisocyanato-2,3,5,6-tetramethylbenzene, 1,4-diisocyanatomethyl-2,3,5,6-tetramethylbenzene, 4,4'-diisocyanatodiphenyl, 4,4'-diisocyanato-3,3'-dichlorodiphenyl, 4,4'-diisocyanato-3,3'-dimethoxydiphenyl, 4,4'-diisocyanato-3,3'-dimethyldiphenyl, 4,4'-diisocyanato-3,3'-diphenyldiphenyl, 4,4'-diisocyanatodiphenylmethane, 4,4'-diisocyanato-3,3',5,5'-tetramethyldiphenylmethane, 4,4'-diisocyanato-2,2',3,3',5,5',6,6'-octamethyldiphenylmethane, naphthylene-1,5-diisocyanate, toluenediisocyanates, such as toluene-2,4- and 2,6-diisocyanate, N,N'-(4,4'-dimethyl-3,3'-diisocyanatodiphenyl)-uretdione, m-xylylenediisocyanate, as well as any mixtures of these compounds. Additional suitable isocyanates are described in the cited article in the Annalen on page 122f. As a rule, the technically readily obtainable aliphatic, cycloaliphatic, or aromatic diisocyanates, as well as mixtures of their isomers are especially preferred.

The isocyanurates containing isocyanate groups produced in accordance with the invention are valuable intermediates for the production of polyurethanes.

EXAMPLE A1

232 grams of dipropyleneglycol (DPG) and 90 g of glacial acetic acid were charged into a 1-liter three-necked flask provided with stirrer, reflux condenser and dropping funnel. Trimethylamine was then introduced into this mixture until a weight increase of 87 g was obtained. Subsequently, 87 g of propyleneoxide (PO) were slowly added at 25° C. while stirring vigorously. After the addition of PO was terminated, the mixture was stirred over night at room temperature and then the unconverted volatile materials were removed under vacuum during 6 hours at 45° C. A residue remained having a weight of 484 g.

Using the above described process, additional compounds were produced whose synthesis is summarized in Table I below (Examples A2–A8).

TABLE I

| Example | Amine | Acid | Alkylene oxide | Solvent | NMR - ANALYSIS Mole-% quaternary nitrogen | Mole % teriary nitrogen | Mole % dipropylene glycol |
|---|---|---|---|---|---|---|---|
| A2 | trimethylamine | acetic acid | propylene oxide | dipropylene glycol | 46.5 | 0.00 | 53.5 |
| A3 | trimethylamine | formic acid | propylene oxide | dipropylene glycol | 41.5 | 0.00 | 58.5 |
| A4 | quinuclidine | acetic acid | glycidol | dipropylene glycol | 38.1 | 0.00 | 61.9 |
| A5 | N,N'—endoethylene piperazine | formic acid | propylene oxide | none | 55.0–29.0 mono | 0.00 | 16.0 |
| A6 | N—methylmorpholine | cyanoacetic acid | propylene oxide | dipropylene glycol | 30.6 | 22.2 | 47.0 |
| A7 | trimethylamine | dichloroacetic acid | ethylene oxide | water and methanol | 100 | 0.00 | 0.00 |
| A8 | trimethylamine | 2-ethylhexanoic acid | propylene oxide | dipropylene glycol | 59.0 | 0.00 | 41.0 |

B. Trimerization of diisocyanates with the catalysts described under A.

The continuous production of partially trimerized diisocyanates (up to approximately 35–45% conversions) was effected in a coiled tube reactor at 60°–120° C. and with a residence time of approximately 1–7 minutes. The coil reactor consisted of two heating zones and one cooling zone whereby in the first heating zone the starting materials (diisocyanates+catalysts) were initially preheated to the reaction temperature, in the second zone the reaction temperature was maintained at the reaction temperature through partial removal of the reaction heat, and in the cooling zone, the reaction mixture was cooled to temperatures below 40° C.

The diisocyanate/catalyst mixtures, which had been thoroughly stirred in a pre-mixer, entered the heating coil which was heated with oil of 85°–90° C. at a temperature of approximately 30° C. After having passed through the heating coil with a residence time of approximately 0.8–1.5 minutes the diisocyanate-catalyst mixtures had a temperature of approximately 80°–85° C. and were already trimerized to the extent of 7.5–10%.

The further conversion of the diisocyanates from 7.5–10% to a maximum of 33–45% was then effected at 80°–90° C. In this instance, approximately 84 kilojoules have to be removed per kilogram output. The reaction mixture was subsequently cooled to a temperature below 40° C. in the appended cooling coil.

The coil combination used for these tests for the production of partially trimerized diisocyanates had the following dimensions:

|  | Inner diameter (mm) | Length (m) | Capacity (liters) |
|---|---|---|---|
| Heating coil | 10 | 7 | 0.6 |
|  | 6 | 3 |  |
| Reaction coil | 14 | 9 | 1.4 |
| Cooling coil | 14 | 18 | 2.8 |

After leaving the cooling coil, the reaction mixture had an NCO content which corresponds to a diisocyanate conversion of approximately 35-45% with a residence time given in the Tables II a+b below.

The conversion into the trimerized form can be undertaken with continuous monitoring of the refractive indexes. Refractive indexes for IPDI in the range from about 1.4950-14990 correspond approximately to a conversion of the order of magnitude of 35-45%.

The separation of the unconverted diisocyanates from the trimerized form was carried out continuously under vacuum in a preliminary and a main evaporator stage and the distillates were in each case recycled to the trimerization.

TABLE IIa

Continuous trimerization of various diisocyanates

| Example | isocyanate | Catalyst (% by weight) based on diisocyanate used % by weight | catalyst of example | Throughput kg/h | Residence time (min.) in the reaction coil | Temperature (°C.) of the Heating Zone HZ HZ 1 | HZ 2 | HZ 3 | Refractive index $n_D^{25}$ after HZ 1 | HZ 2 | HZ 3 | Workup of the partially trimerized diisocyanate by thin-film distillation-composition of residue % NCO | Monomer content |
|---|---|---|---|---|---|---|---|---|---|---|---|---|---|
| B1 | TMDI | 0.05 | A1 | 40 | 2.10 | 86 | 85 | 33 | 1.4690 | 1.4770 | 1.4775 | 16.9 | <0.6 |
| B2 | TMDI | 0.03 | A2 | 60 | 1.39 | 87 | 86 | 32 | 1.4683 | 1.4765 | 1.4770 | 16.8 | <0.6 |
| B3 | TMDI | 0.02 | A8 | 50 | 1.76 | 87 | 86 | 32 | 1.4672 | 1.4661 | 1.4755 | 17.0 | <0.7 |
| B4 | OCN—(CH$_2$)$_6$—NCO | 0.04 | A1 | 70 | 1.20 | 86 | 86 | 33 | 1.4570 | 1.4661 | 1.4668 | 21.0 | <0.5 |
| B5 | OCN—(CH$_2$)$_6$—NCO | 0.02 | A2 | 45 | 1.86 | 87 | 86 | 32 | 1.4564 | 1.4653 | 1.4658 | 21.4 | <0.5 |
| B6 | OCN—(CH$_2$)$_6$—NCO | 0.05 | A3 | 49 | 1.77 | 88 | 87 | 33 | 1.4573 | 1.4668 | 1.4676 | 20.9 | <0.6 |
| B7 | OCN—(CH$_2$)$_6$—NCO | 0.06 | A2 | 45 | 1.86 | 87 | 86 | 32 | 1.5187 | 1.5261 | 1.5270 | 11.3 | <0.5 |
| B8 | 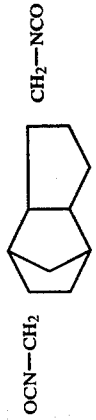 | 0.07 | A3 | 60 | 1.39 | 87 | 86 | 33 | 1.1593 | 1.5266 | 1.5273 | 11.5 | <0.6 |
| B9 | 20 wt. % 2,6- 80 wt. % 2,4-  | 0.08 | A3 | 75 | 1.12 | 87 | 86 | 33 | 1.5198 | 1.5273 | 1.5283 | 11.5 | <0.6 |
| B10 | 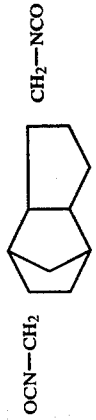 | 0.01 / 0.02 / 0.01 | A1 / A2 / A8 | 60 / 65 / 60 | 1.39 / 1.29 / 1.39 | 87 / 87 / 86 | 86 / 86 / 85 | 33 / 32 / 32 | 1.5712 / 1.5729 / 1.5701 | 1.5781 / 1.5794 / 1.5778 | 1.5789 / 1.5803 / 1.5781 | 21.5 / 21.0 / 21.3 | <0.7 / <0.6 / <0.7 |
| B11 | OCN—CH$_2$—⟨H⟩—⟨H⟩—CH$_2$—NCO | 0.07 | A3 | 60 | 1.39 | 86 | 86 | 32 | 1.4901 | 1.4961 | 1.4970 | 19.5 | <0.7 |
| B12 | OCN—(CH$_2$)$_4$—C(H)(CH$_3$)—(CH$_2$)$_4$—NCO | 0.05 | A1 | 70 | 1.20 | 87 | 86 | 33 | 1.4610 | 1.4695 | 1.4706 | 15.4 | <0.6 |
| B13 | 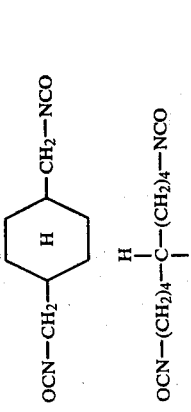 | 0.08 | A2 | 65 | 1.29 | 88 | 87 | 33 | 1.5025 | 1.5092 | 1.5097 | 14.3 | <0.6 |

TABLE IIb

Continuous trimerization of IPDI as a function of catalyst and residence time

| Example | Catalyst % by weight | Based on IPDI of example | Output kg/h | Residence time (min.) in reaction coil | Temperature (°C.) Heating Zone - HZ | | | Refractive index $n_D^{25}$ after | | | Workup of partially trimerized IPDI by thin-film distillation Composition of residue | |
|---|---|---|---|---|---|---|---|---|---|---|---|---|
| | | | | | HZ 1 | HZ 2 | HZ 3 | HZ 1 | HZ 2 | HZ 3 | % NCO | Monomer Content % |
| 14 | 0.080 | A1 | 45 | 1.86 | 85 | 85 | 34 | 1.4900 | 1.4961 | 1.4970 | 17.38 | 0.5 |
| 15 | 0.079 | A2 | 40 | 2.10 | 94 | 84 | 38 | 1.4905 | 1.4948 | 1.4952 | 17.50 | 0.5 |
| 16 | 0.062 | A2 | 60 | 1.39 | 85 | 85 | 34 | 1.4890 | 1.4958 | 1.4964 | 17.45 | 0.2 |
| 17 | 0.070 | A2 | 60 | 1.39 | 86 | 87 | 35 | 1.4888 | 1.4974 | 1.4981 | 17.25 | 0.3 |
| 18 | 0.081 | A2 | 75 | 1.12 | 86 | 87 | 39 | 1.4859 | 1.4934 | 1.4939 | 17.51 | 0.2 |
| 19 | 0.080 | A2 | 70 | 1.20 | 86 | 86 | 38 | 1.4870 | 1.4952 | 1.4965 | 17.3 | 0.3 |
| 20 | 0.055 | A2 | 40 | 2.10 | 80 | 80 | 32 | 1.4878 | 1.4959 | 1.4962 | 17.44 | 0.4 |
| 21 | 0.065 | A3 | 70 | 1.20 | 86 | 86 | 34 | 1.4891 | 1.4869 | 1.4975 | 17.43 | 0.4 |
| 22 | 0.057 | A8 | 40 | 2.10 | 85 | 85 | 33 | 1.4880 | 1.4956 | 1.4960 | 17.40 | 0.3 |
| 23 | 0.057 | A8 | 60 | 1.39 | 86 | 86 | 33 | 1.4870 | 1.4952 | 1.4958 | 17.42 | 0.4 |
| 24 | 0.062 | A8 | 65 | 1.29 | 87 | 86 | 34 | 1.4882 | 1.4960 | 1.4963 | 17.40 | 0.5 |

2. Batchwise preparation

EXAMPLE 25

50 Parts by weight of 2,2,4 or 2,4,4-trimethylhexamethylenediisocyanate-1,6 (1:1 mixture=TMDI) and 0.02 parts by weight of the catalyst of Example A2 of Table I were mixed together while being vigorously stirred and were subsequently heated to 75° C. After a heating period of approximately 50 minutes, the NCO content of the reaction mixture amounted only to 31%. In order to remove the unconverted TMDI, the reaction mixture was distilled at 180° C./2.14 Pa in a thin-film evaporator. The reaction product (residue of the thin-film evaporation) had an NCO content of 16.9% and a monomer content of <0.6%. The viscosity of the isocyanatoisocyanurate amounted to 540 Pa.s at 40° C., 12 Pa.s at 60° C., 3.3 Pa.s at 80° C., 0.02 Pa.s at 100° C., and 90 P.as at 40° C.

EXAMPLE 26

50 Parts by weight of TMDI (see Example 25) and 0.05 parts by weight of the catalyst of Example A8 of Table I were mixed together while being vigorously stirred and were subsequently heated to 70° C. After a heating period of approximately 40 minutes, the NCO content of the reaction mixture amounted to 32.1%. In order to remove the unconverted TMDI, the reaction mixture was also distilled at 180° C./2.14 Pa in a thin film evaporator. The reaction product (residue of the thin film evaporation) had an NCO content of 17.1% and a monomer content of <0.7%.

EXAMPLE 27

100 Parts by weight of hexamethylenediisocyanate and 0.03 parts by weight of the catalyst of Example A3 of Table I were mixed together while being vigorously stirred and were subsequently heated to 80° C. After a heating period of 60 minutes, the NCO content of the reaction mixture amounted to 37%. In order to remove the unconverted hexamethylenediisocyanate, the reaction mixture was distilled at 140° C./15.7 Pa in a thin-film evaporator. The reaction product (residue of the thin-film evaporation) had an NCO content of 20.8% and a monomer content of <0.6%; its viscosity amounted to 14 Pa.s at room temperature, 3.5 Pa.s at 40° C. and 1 Pa.s at 60° C.

EXAMPLE 28

100 Parts by weight of 3(4), 8(9)-diisocyanatomethyltricyclo[5.2.1.0$^{2,6}$]decane (TCDI) and 0.04 parts by weight of the catalyst of Example 25 were mixed together while being vigorously stirred and were subsequently heated to 75° C. After a heating period of 50 minutes, the NCO content of the reaction mixture amounted to 27.5%. The isolation of the isocyanatoisocyanurate was carried out by thin-film evaporation as in the Examples 25-27.

Residue of the tin-film evaporation:
% NCO: 11.6
Monomer content (%): 0.7
Viscosity Pa.s
    at 120° C.: 400
    at 140° C.: 140

EXAMPLE 29

100 Parts by weight of 1,4-diisocyanatomethylcyclohexane were thoroughly mixed with 0.02 parts by weight of the catalyst of Example A2 of Table I and were heated to 80° C. After a heating period of 60 minutes, the NCO content of the reaction mixture amounted to 33%. The isolation of the isocyanatoisocyanurate was carried out by thin film evaporation as in Examples 25-27.

Residue of the thin film evaporation:
% NCO: 19.5
Monomer content (%): 0.7
Viscosity Pa.s
    at 120° C.: 4.3
    at 140° C.: 1.0

EXAMPLE 30

50 Parts by weight of isophoronediisocyanate and 0.025 parts by weight of the catalyst of Example A2 of Table I were mixed together while being vigorously stirred and were subsequently heated to 80°. After a heating period of approximately 60 minutes, the NCO content of the reaction mixture amounted to 30.5%. In order to remove the unconverted IPDI, the reaction mixture was distilled at 190° C./6.7 Pa in a thin film evaporator. The reaction product (residue of the thin film evaporation) had an NCO content of 17.4% and a monomer content of <0.6%. The melting point of the isocyanatoisocyanurate amounted to 86°-90° C., and the viscosity was 140 Pa.s at 120° C. and 41 Pa.s at 140° C.

EXAMPLE 31

500 Parts by weight of IPDI and 0.3 parts by weight of the catalyst of Example A3 of Table I were mixed together while being vigorously stirred and were subsequently heated to 70° C. After a heating period of approximately 20 minutes, the NCO content of the reaction mixture amounted to 29.8%. The reaction mixture was then subjected to the same treatment as in Example 30.

The isocyanatoisocyanurate of the IPDI, freed from the IPDI, had an NCO content of 17.3% and a monomer content of <0.7%.

EXAMPLE 32

50 Parts by weight of IPDI and 0.05 parts by weight of the catalyst of Example A8 of Table I were mixed together while being vigorously stirred and were subsequently heated to 70° C. After a reaction period of 15 minutes, the NCO content of the reaction mixture amounted to 30.4%. The reaction mixture was then subjected to the same treatment as in Examples 30–31.

The reaction product (residue of the thin-film evaporation) contained 17.2% NCO and had a monomer content of <0.5%.

The production of the trimerization catalysts is known. In the customary procedures for producing N-(hydroxyalkyl) ammonium salts, equal amounts of a tertiary amine, a carbonic acid and an alkylene oxide are mixed, preferably in a suitable solvent, such as dipropylene glycol. The reaction is then carried out at a temperature within the range of 25°–60° C. and at approximately atmospheric pressure. However, higher pressures, for example, pressures up to 35 atmospheres can also be used. Example A1 illustrates a typical synthesis procedure. The same procedure has been used in the additional Examples A2–A8 wherein slight modifications are also possible with regard to the temperature, the selection of the solvent or the use of the solvent.

Tertiary amines suitable for reacting with the alkylene oxide and carbonic acid to produce the catalysts used in accordance with the invention are those which have one to three hydroxyalkyl groups and one or several alkyl groups, cycloalkyl groups or aryl groups bound to the nitrogen atom. Among others, especially preferred tertiary amines of this kind are trimethylene, N-dimethyl-N-hydroxyethylamine, N-benzyl-N-dimethylamine, triethylamine, N-di-(hydroxethyl)-N-phenylamine, triethanolamine, N-cyclohexyl-N-dimethylamine, N-methylmorpholine, N,N'-endoethylenepiperazine-(1,4-diazabicyclooctane-[2.2.2]) and quinuclidine.

Of the alkylene oxides which can be reacted with the tertiary amines, the aliphatic ones especially are to be emphasized, such as ethylene oxide, propylene oxide, 1,2-butylene oxide, butadiene dioxide, methylglycidyl ether, ehtylglycidyl ether, propylglycidyl ether, alkylglycidyl ether, n-butylglycidyl ether, 2-ethylhexylglycidyl ether, diglycidyl ether and the like, glycidol and alkylene oxides having longer chains (which are commercially available under the name of "Nedox" from Ashland Chemical Company) of the general formula of

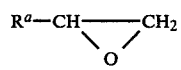

in which $R^a$ represents a long-chained alkyl group or a mixture of such groups having up to 15 carbon atoms, the cycloaliphatic ones, such as cyclohexene oxide, cyclopentadiene oxide, vinylcyclohexene dioxide, dicyclopentadiene dioxide, as well as the aromatic epoxides, such as styrene oxide, phenylglycidyl ether and the like. The anion of the desired quaternary ammonium salt can be any carbonic acid. Thus, the compounds of the mentioned general formula are obtained with fatty acids having short or long chains, with substituted aliphatic acids and with aromatic carbonic acids. Especially preferred acids are formic acid, acetic acid, cyanoacetic acid, chloracetic acid, hexanoic acid as well as the linear or branched heptanoic acids, octanoic acids, 2-ethylhexanoic acid, decanoic acids and hexadecanoic acids; neo-acids, such as 3,3-dimethylbutanoicacid and the like.

By reacting the various quaternary ammonium alcoholates or phenolates with $CO_2$, alkyl carbonates or phenyl carbonates also can be obtained.

We claim:

1. In a process for trimerization of diisocyanates in the presence of a catalyst comprising quaternary ammonium salts of organic acids having the formula:

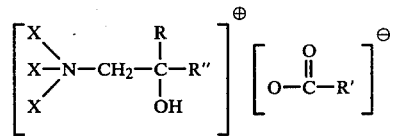

wherein X represents the same or different radicals selected from the group consisting of $C_1$-$C_{20}$ alkyl, $C_3$-$C_8$ cycloalkyl, and $C_2$-$C_{20}$ aralkyl; two X radicals taken together with at least one other heteroatom forming a hetero-ring and three X radicals taken together with the quarternary nitrogen atoms forming a heteroring through a common heteroatom such that said heterocyclic ring structure is selected from the group consisting of triethylene diamine, methyl triethylene diamine, quinuclidine, N-methylmorpholine, N-ethylmorpholine and N,N'-dimethylpiperazine; R is alkyl, cycloalkyl or aralkyl, R" is R or hydrogen; R+R" together form a $C_1$-$C_{12}$ alkyl radical; R' is hydrogen, hydroxyl or a $C_1$-$C_{12}$ alkyl radical optionally containing a $CH_{(3-b)}Z_b$ group, wherein b=1 to 3 and Z is OH, the improvement comprising:

reacting said diisocyanate with said catalyst in an amount of 0.02–0.1% by weight calculated on the weight of the compound to be trimerized at a temperature ranging from 40°–120° C.

2. The process according to claim 1, wherein said trimerization reaction is conducted at a temperature in the range of 60° C.–90° C.

3. A process according to claim 1, characterized in that the trimerization is carried out up to a conversion of 45%.

4. A process according to claim 1 or 2, characterized in that the trimerization is carried out continuously in a coolable tube-shaped reactor with simultaneous addition of monomeric isocyanate containing catalyst.

5. A process according to claims 1 or 3, characterized in that the unconverted monomeric isocyanate is removed by means of a thin-film distillation.

6. A process according to claims 1 or 3, characterized in that aromatic diisocyanates are trimerized.

7. A process according to claims 1 or 3, characterized in that aliphatic diisocyanates are trimerized.

8. A process according to claims 1 or 3, characterized in that cycloaliphatic diisocyanates are trimerized.

9. A process according to claim 8, characterized in that the cycloaliphatic diisocyanate is isophorone diisocyanate.

* * * * *